(12) United States Patent
Xiang et al.

(10) Patent No.: US 6,797,730 B2
(45) Date of Patent: Sep. 28, 2004

(54) PEPTIDE DEFORMYLASE INHIBITORS

(75) Inventors: Jia-Ning Xiang, Palo Alto, CA (US); Siegfried B. Christensen, IV, Collegeville, PA (US); Jinhwa Lee, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/469,515
(22) PCT Filed: Mar. 1, 2002
(86) PCT No.: PCT/US02/06260
§ 371 (c)(1), (2), (4) Date: Feb. 18, 2004
(87) PCT Pub. No.: WO02/070653
PCT Pub. Date: Sep. 12, 2002

(65) Prior Publication Data
US 2004/0133001 A1 Jul. 8, 2004

Related U.S. Application Data

(60) Provisional application No. 60/272,445, filed on Mar. 1, 2001.

(51) Int. Cl.$^7$ .................. A61K 31/19; C07C 271/00
(52) U.S. Cl. ............................... 514/575; 560/24
(58) Field of Search ........................... 560/24; 514/575

(56) References Cited

FOREIGN PATENT DOCUMENTS

GB  WO 02/50081 A2 *  6/2002
WO  WO 01/10834       2/2001

* cited by examiner

Primary Examiner—Johann Richter
Assistant Examiner—Paul A. Zucker
(74) Attorney, Agent, or Firm—Soma G. Simon; Mary McCarthy; Charles M. Kinzig

(57) ABSTRACT

Novel PDF inhibitors and novel methods for their use are provided.

4 Claims, No Drawings

PEPTIDE DEFORMYLASE INHIBITORS

This application is the National Stage of International Application No. PCT/US02/06260 filed Mar. 1, 2002, which claims the benefit of Provisional application No. 60/272,445 filed Mar. 1, 2001.

FIELD OF THE INVENTION

The present invention relates to the use of novel antibacterial compounds, and pharmaceutical compositions containing these compounds as peptide deformylase inhibitors.

BACKGROUND OF THE INVENTION

Bacterial initiator methionyl tRNA is modified by methionyl tRNA formyltransferase (FMT) to produce formylmethionyl tRNA The formyl methionine (f-met) is then incorporated at the N-termini of newly synthesized polypeptides. Polypeptide deformylase (PDF or Def) then deformylates primary translation products to produce N-methionyl polypeptides. Most intracellular proteins are further processed by methionine aminopeptidase (MAP) to yield the mature peptide and free methionine, which is recycled. PDF and MAP are both essential for bacterial growth, and PDF is required for MAP activity. This series of reactions is referred to as the methionine cycle (Figure 1).

Figure 1. The methionine cycle.

To date, polypeptide deformylase homologous genes have been found in bacteria, in chloroplast-containing plants, in mice and in humans. The plant proteins are nuclear encoded but appear to carry a chloroplast localisation signal. This is consistent with the observation that chloroplast RNA and protein synthesis processes are highly similar to those of eubacteria While there is limited information on protein expression of mammalian PDF gene homologs (Bayer Aktiengesellschaft, Pat. WO2001/42431), no functional role for such proteins has been demonstrated to date (Meinnel, T., Parasitology Today 16(4), 165–168, 2000).

Polypeptide deformylase is found in all eubacteria for which high coverage genonic sequence information is available. Sequence diversity among PDF homologs is high, with as little as 20% identity between distantly related sequences. However, conservation around the active site is very high, with several completely conserved residues, including one cysteine and two histidines which are required to coordinate the active site metal (Meinnel, T. et al., 1997, Journal of Molecular Biology, 267, 749–761).

PDF is recognized to be an attractive antibacterial target, as this enzyme has been demonstrated to be essential for bacterial growth in vitro (Mazel, D. et al., EMBO J. 13 (4), 914–923, 1994), is not believed to be involved in eukaryotic protein synthesis (Rajagopalan et al., J. Am. Chem. Soc. 119, 12418–12419, 1997), and is universally conserved in prokaryotes (Kozak, M., Microbiol. Rev. 47, 1–45, 1983). Therefore PDF inhibitors can potentially serve as broad spectrum antibacterial agents.

SUMMARY OF THE INVENTION

The present invention involves novel antibacterial compounds represented by Formula (1) hereinbelow and their use as PDF inhibitors.

DETAILED DESCRIPTION OF THE INVENTION

The compounds useful in the present methods are selected from Formula (1) hereinbelow:

(1)

wherein:
R is selected from the group consisting of $C_{1-6}$ alkyl, —$CH_2Ar$, and Ar;
R1 is selected from the group consisting of $C_{1-6}$ alkyl, —$C_{1-4}$ alkyl-Ar', and Ar';
R2 is selected from the group consisting of hydrogen, and $C_{1-6}$ alkyl;
Ar is selected from the group consisting of phenyl, furyl, and thienyl, all of which optionally substituted by one or more $Z_1$ groups;
Ar' is selected from the group consisting of phenyl, naphthyl, furyl, pyridyl, thienyl, thiazolyl, isothiazolyl, pyrazolyl, triazolyl, tetrazolyl, imidazolyl, imidazolidinyl, benzofuranyl, indolyl, thiazolidinyl, isoxazolyl, oxadiazolyl, thiadiazolyl, morpholinyl, piperidinyl, piperazinyl, pyrrolyl, and pyrimidyl; all of which optionally substituted by one or more $Z_2$ groups;
$Z_1$ is independently is selected from the group consisting of $C_{1-3}$ alkyl, CN, F, Cl, Br, and I;
$Z_2$ is independently is selected from the group consisting of $C_{1-4}$ alkyl, $C_{1-4}$ alkoxy, —$(CH_2)_nC(O)OR2$, —$C(O)NRR2$, —CN, —$(CH_2)_nOH$, —$NO_2$, F, Cl, Br, I, —$NRR_2$, and —$NHC(O)R2$;
n is 0 to 4;
or a salt, solvate, or physiologically functional derivative thereof.

In this invention the most preferred absolute configuration of compounds of the formula (1) is indicated below:

As used herein, "alkyl" refers to an optionally substituted hydrocarbon group joined together by single carbon-carbon bonds. The alkyl hydrocarbon group may be linear, branched or cyclic.

Preferred compounds useful in the present invention are selected from the group consisting of:
N-{(R)-1-[(Formyl-hydroxy-amino)methyl]-2-phenylethyl}carbamic acid tert-butyl ester, N-{(S)-1-[(Formyl-hydroxy-amino)methyl]-2-phenyl-ethyl}carbamic acid tert-butyl ester, N-[(S)-1-Benzyl-2-(formyl-hydroxy-amino)-ethyl]-carbamic acid 1,1-dimethyl-propyl ester, and N-[(S)-1-Benzyl-2-(formyl-hydroxy-amino)-ethyl]-carbamic acid methyl ester.

Also included in the present invention are pharmaceutically acceptable salts and complexes, such as the hydrochloride, hydrobromide and trifluoroacetate salts, and the sodium, potassium, and magnesium salts. The compounds of the present invention may contain one or more asymmetric carbon atoms and may exist in racemic and optically active forms. All of these compounds and diastereomers are contemplated to be within the scope of the present invention.

The compounds and processes of the present invention will be better understood in connection with the following synthetic schemes, which are merely illustrative of the methods by which the compounds of the invention may be prepared and are not intended to limit the scope of the invention as defined in the appended claims.

The present invention provides compounds of Formula (1)

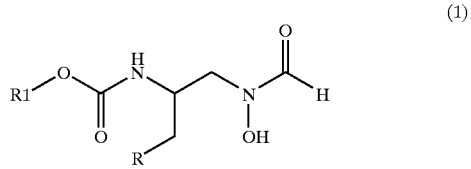
(1)

that can be prepared by a process consisting of reacting a compound of Formula (2)

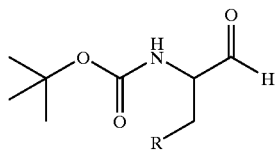
(2)

with O-benzylhydroxylamine hydrochloride in an appropriate solvent, such as dry pyridine, at room temperature, followed by removing the solvent. The crude mixture is then redissolved in an appropriate solvent, such as glacial acetic acid, and treated with a reducing agent, such as sodium cyanoborohydride, to provide an amine of Formula (3).

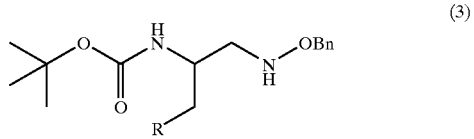
(3)

An amine of Formula (3) is treated with a formylating agent, such as a solution of premixed formic acid and acetic anhydride at an appropriate temperature, such as 0° C., to afford a compound of Formula (4).

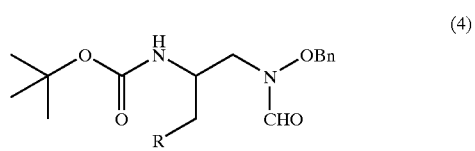
(4)

Cleavage of the benzyl protecting group in a compound of Formula (4) under hydrogen atmosphere in the presence of a palladium catalyst, such as palladium on activated carbon, gives a compound of Formula (1), wherein R1=t-Bu.

Treatment of a compound of Formula (4) with an acid, such as trifluoroacetic acid, affords a primary amine of Formula (5).

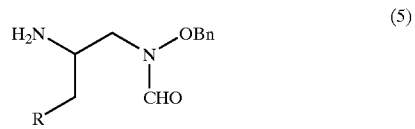
(5)

Reaction of an amine of Formula (5) with an appropriate agent, such as (R1OCO)$_2$O (6), wherein R1 is not t-Bu, in the presence of a base, such as triethylamine, results in a carbamate of Formula (7).

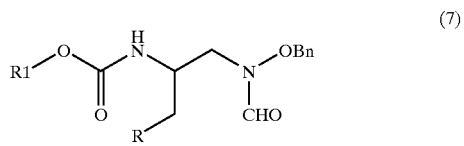
(7)

Conversion of a compound of Formula (7) to a compound of Formula (1) wherein R1 is not t-Bu, is readily achieved using the same conditions under which (4) is converted to (1) wherein R1=t-Bu.

The enantiomers of Compound (1):

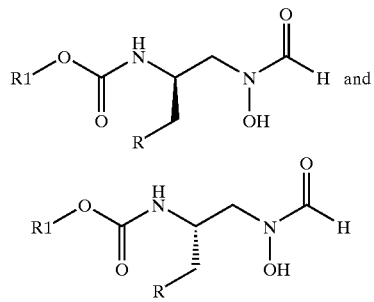

can be prepared by using the same protocol described above, starting from the (R) and (S) isomer, respectively, of the compound of Formula (2).

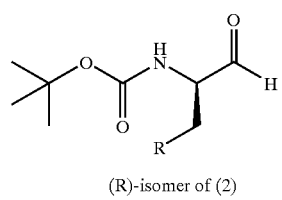

(R)-isomer of (2)

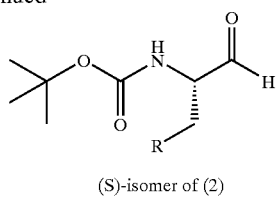

(S)-isomer of (2)

Alternatively, any racemates can be resolved at the level of any intermediate during the synthesis or at the level of the final product using, for example, a chiral chromatography method, to provide compound (1) in each of two enantiomeric forms.

SYNTHETIC EXAMPLES

The invention will now be described by reference to the following examples which are merely illustrative and are not to be construed as a limitation of the scope of the present invention. All temperatures are given in degrees centigrade, and all solvents are highest available purity unless otherwise indicated.

Example 1

N-{(R)-1-[(Formylhydroxyamino)methyl]-2-phenyl-ethyl}-carbamic acid tert-butyl ester.
N-[(R)-1-(Benzvloxvaminomethyl)-2-phenl-ethyl]-carbamic acid tert-butyl ester.

The mixture of (R)-(+)-2-(tert-butoxycarbonylamino)-3-phenylpropanal (1.09 g, 4.37 mmol) and O-benzylhydroxylamine hydrochloride (0.91 g, 5.68 mmol) in dry pyridine (5 mL) was stirred for 2 hours at room temperature. Removal of solvent gave the oxime as a crude compound. To a solution of the oxime in glacial acetic acid (5 mL) was added $NaBH_3(CN)$ (0.47 g, 7.43 mmol) at room temperature. The reaction mixture was stirred for 2 hours at room temperature, and the reaction was then quenched with water (15 mL) and extracted using ether (20 mL×2). The combined organic layers were washed with brine, and dried over $MgSO_4$. Removing the solvent under reduced pressure yielded 1.56 g (90%) of the title compound. $^1H$ NMR (400 MHz, CDCl3): δ 7.42–7.19 (m, 10H), 4.83 (br s, 1H), 4.72 (s, 2H), 4.05 (br s, 1H), 3.06 (dd, J=13.5, 4.2 Hz, 1H), 2.90–2.79 (m, 3H), 1.42 (s, 9H). MH+357.
N-{(R)-1-[(Benzvloxvformylamino)methyl]-2-phenyl-ethyl}-carbamic acid tert-butyl ester.

To a cold mixture of formic acid (2.3 g, 73.0 mmol) and acetic anhydride (0.56 mL, 6.0 mmol) was added dropwise [(R)-1-(Benzyloxyaminomethyl)-2-phenyl-ethyl)-carbamic acid tert-butyl ester (0.20 g, 0.56 mmol) in dichloromethane (2.8 mL) at 0° C. The reaction mixture was stirred at 0° C. for 3 hours, and then treated with saturated aq. $NaHCO_3$ (5 mL). The aqueous layer was extracted with dichloromethane (10 mL×2). The organic extracts were washed with water and brine, and dried over $MgSO_4$. After removal of the solvent under reduced pressure, purification by flash column chromatography using an eluting system of hexane/EtOAc (2:1) yielded 0.19 g (86%) of the title compound $^1H$ NMR (400 MHz, CDCl$_3$): δ 8.14 (br s, 1H), 7.32–7.07 (m, 10H), 4.90–4.67 (m, 2H), 4.15 (m, 1H), 3.74 (m, 1H), 3.36 (m, 1H), 2.78 (m, 1H), 2.68 (m, 2H), 1.32 (m, 9H). MH+385.
N-{(R)-1-[Formylhtdrixtamino)methyl]-2-phenyl-ethyl}-carbamic acid tert-butyl ester.

To a solution of N-{(R)-1-(Benzyloxyformylamino) methyl]-2-phenyl-ethyl}-carbamic acid tert-butyl ester (67 mg, 0.174 mmol) in EtOH (4 mL) was added 10% Pd/C (14 mg). The reaction mixture was subjected to hydrogenation overnight at room temperature. After the reaction was completed, the reaction mixture was filtered through a pad of Celite, and washed with EtOH (5 mL×3). Removal of the solvent provided the crude product, which was further purified by HPLC to yield 35 mg (68%) of the title compound. $^1H$ NMR (400 MHz, CHCl$_{13}$): δ 8.95 (br s, 1H), 8.36 (s, 1H), 7.37–7.20 (m, 5H), 4.77 (m, 1H), 4.24 (m, 1H), 4.05 (m, 1H), 3.09 (m, 1H), 2.86 (m, 2H), 1.42 (s, 9H). MH+294.

Example 2

N-{(S)-1-[(Formylhydroxyamino)methyl]-2-phenethyl}-carbamic acid tert-butyl ester.

Following the procedures of Example 1 except that (S) (−)-2-(tert-butoxycarbonyl amino)-3-phenylpropanal was used in place of (R)-(+)-2-(tert-butoxycarbonyl amino)-3-phenylpropanal. After debenzylation as described in 1, purification by preparative HPLC yielded 70 mg (50%) of the title compound. $^1H$ NMR (400 MHz, CHCl$_3$): δ 8.95 (br s, 1H), 8.36 (s, 1H), 7.37–7.20 (m, 5H), 4.77 (m, 1H), 4.24 (m, 1H), 4.05 (m, 1H), (m, 1H), 2.86 (ma, 2H), 1.42 (s, 9M). MH+294.

Example 3

N-[(S)-1-Benzyl-2-(formyl-hydroxy-amino)-ethyl]-carbamic acid 1,1-dimethyl-propyl ester.
MH+309.

Example 4

N-[(S)-1-Benzyl-2(formyl-hydroxy-amino)-ethyl]-carbamic add methyl ester.
MH+253.

In order to use a compound of the Formula (1) or a pharmaceutically acceptable salt thereof for the treatment of humans and other mammals it is normally formulated in accordance with standard pharmaceutical practice as a pharmaceutical composition.

The present compounds are useful for the treatment of bacterial infections including but not limited to respiratory tract infections and/or Gram positive infections.

Compounds of Formula (1) and their pharmaceutically acceptable salts may be administered in a standard manner for antibiotics, for example orally, parenterally, sublingually, dermnally transdermally, rectally, via inhalation or via buccal administration.

Compositions of Formula (1) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and tansdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula (1) or a pharmaceutically acceptable salt thereof calculated as the free acid. Each dosage unit for intranasal administration contains suitably 1–400 mg and preferably 10 to 200 mg per person. A topical formulation contains suitably 0.01 to 5.0% of a compound of Formula (I).

The daily dosage regimen for oral administration is suitably about 0.01 mg/Kg to 40 mg/Kg, of a compound of Formula(I) or a pharmaceutically acceptable salt thereof calculated as the free acid. The daily dosage regimen for parenteral administration is suitably about 0.001 mg/Kg to 40 mg/Kg, of a compound of Formula (1) or a pharmaceutically acceptable salt thereof calculated as the free acid, the daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (1) are demonstrated by the following test:

Biological Assay

S. aureus or E. coli PDF activity is measured at 25° C., using a continuous enzyme-linked assay developed by Lazennec & Meinnel, (1997) "Formate dehydrogenase-coupled spectrophotometric assay of peptide deformylase" Anal. Biochem 244, pp.180–182, with minor modifications. The reaction mixture is contained in 50 uL with 50 mM potassium phosphate buffer (pH 7.6), 15 mM NAD, 0.25 U formate dehydrogenase. The substrate peptide, f-Met-Ala-Ser, is included at the $K_M$ concentration. The reaction is triggered with the addition of 10 nM Def1 enzyme, and absorbance is monitored for 20 min at 340 nm.

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically" (incorporated by reference herein). The compound was tested in serial twofold dilutions ranging from 0.06 to 64 mcg/ml. A panel of 12 strains were evaluated in the assay. This panel consisted of the following laboratory strains: Staphylococcus aureus Oxford, Staphylococcus aureus WCUH29, Enterococcus faecalis I, Enterococcus faecalis 7, Haemophilus influenzae Q1, Haemophilus influenzae NEMC1, Moraxella catarrhalis 1502, Streptococcus pneumoniae 1629, Streptococcus pneumoniae N1387, Streptococcus pneumoniae N1387, E. coli 7623 (AcrABEFD+) and E. coli 120 (AcrAB−). The minimum inhibitory concentration (MIC) was determined as the lowest concentration of compound that inhibited visible growth. A mirror reader was used to assist in determining the MIC endpoint.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to Formula (1):

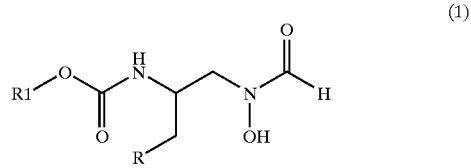

wherein:

R is selected from the group consisting of $C_{1-6}$ alkyl, —CH$_2$Ar, and Ar;

R1 is selected from the group consisting of $C_{1-6}$ alkyl, —C$_{1-4}$ alkyl-Ar', and Ar';

R2 is selected from the group consisting of hydrogen, and $C_{1-6}$ alkyl;

Ar is selected from the group consisting of phenyl, furyl, and thienyl, all of which are optionally substituted by one or more $Z_1$ groups;

Ar' is selected from the group consisting of phenyl, naphthyl, furyl, pyridyl, thienyl, thiazolyl, isothiazolyl, pyrazolyl, triazolyl, tetrazolyl, imidazolyl, imidazolidinyl, benzofuranyl, indolyl, thiazolidinyl, isoxazolyl, oxadiazolyl, thiadiazolyl, morpholinyl, piperidinyl, piperazinyl, pyrrolyl, and pyrimidyl; all of which are optionally substituted by one or more $Z_2$ groups;

$Z_1$ is independently is selected from the group consisting of $C_{1-3}$ alkyl, CN, F, Cl, Br, and I;

$Z_2$ is independently is selected from the group consisting of $C_{1-4}$ alkyl, $C_{1-4}$ alkoxy, —(CH$_2$)$_n$C(O)OR2, —C(O)NRR2, —CN, —(CH$_2$)$_n$OH, —NO$_2$, F, Cl, Br, I, —NRR$_2$, and —NHC(O)R2;

n is 0 to 4;

or a salt, solvate, or physiologically functional derivative thereof.

2. A compound as claimed in claim 1, having the configuration:

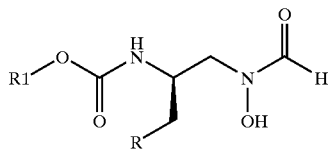

or a salt, solvate, or physiologically functional derivative thereof.

3. A compound according to claim 1 selected from the group consisting of:

N-{(R)-1-[(Formyl-hydroxy-amino)methyl]-2-phenyl-ethyl}carbamic acid tert-butyl ester, N-{(S)-1-[(Formyl-hydroxy-amino)methyl]-2-phenyl-ethyl}carbamic acid tert-butyl ester, N-[(S)-1-Benzyl-2-(formyl-hydroxy-amino)-ethyl]-carbamic acid 1,1 dimethyl-propyl ester, and N-[(S)-1-Benzyl-2-(formyl-hydroxy-amino)ethyl]-carbamic acid methyl ester.

4. A method of treating a bacterial infection by administering to a subject in need of treatment a compound according to claim 1.

* * * * *